(12) United States Patent
Hung et al.

(10) Patent No.: US 7,897,818 B2
(45) Date of Patent: Mar. 1, 2011

(54) METHOD FOR OXIDIZING HYDROCARBONS IN LIQUID PHASE

(75) Inventors: Jui-Tsung Hung, Taipei (TW); Chin-Yi Lee, Taipei (TW); Chia-Jung Tsai, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 12/498,658

(22) Filed: Jul. 7, 2009

(65) Prior Publication Data

US 2010/0036172 A1 Feb. 11, 2010

(30) Foreign Application Priority Data

Aug. 7, 2008 (TW) .............................. 97129999 A

(51) Int. Cl.
*C07C 45/27* (2006.01)
(52) U.S. Cl. .................. 568/357; 568/360; 568/399
(58) Field of Classification Search .................. 568/357, 568/360, 399
See application file for complete search history.

(56) References Cited

U.S. PATENT DOCUMENTS

| 4,341,907 A | 7/1982 | Zelonka |
| 4,658,056 A | 4/1987 | Sipos |

FOREIGN PATENT DOCUMENTS

TW 150309 A 1/1991

*Primary Examiner*—Sikarl A Witherspoon
(74) *Attorney, Agent, or Firm*—Sughrue Mion, PLLC

(57) ABSTRACT

A method of oxidizing hydrocarbons in liquid phase is provided. According to this method, a liquid-phase oxidation reaction of hydrocarbons is carried out by using an organic compound capable of chelating metals as auxiliary agent, represented by formula (II), in the presence of an oxygen-containing gas and a transition metal catalyst. Accordingly, the conversion degree of the hydrocarbon is increased, and the overall yields of products are improved while the selectivity of catalytic oxidation reaction is still high.

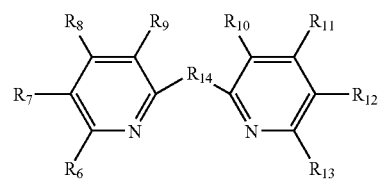

(II)

26 Claims, No Drawings

METHOD FOR OXIDIZING HYDROCARBONS IN LIQUID PHASE

FIELD OF THE INVENTION

The present invention relates to methods for oxidizing hydrocarbons in liquid phase, and more particularly to a method for oxidizing cycloalkane in liquid phase.

BACKGROUND OF THE INVENTION

In the related fields of petrochemical industry, liquid phase oxidation reactions of hydrocarbons play significant roles, in particular, the oxidation of cyclohexane. Cyclohexane is oxidized to give oxidation products, such as cyclohexanone, cyclohexanol, hexanedioic acid, and the like. Among them, cyclohexanone and cyclohexanol are useful starting materials, and can be widely applied to fibers, synthetic rubbers, industrial coatings, medicaments, agrochemicals, organic solvents, etc. In addition, cyclohexanone and cyclohexane can further be converted into caprolactam, and then used to prepare polyamides, such as nylons. Therefore, the oxidation reaction of cyclohexane for producing cyclohexanone and cyclohexanol is very valuable from the industrial point of view.

Commercial processes for oxidizing cyclohexane are typically operated at temperatures within the range of 140 to 170° C. under air pressures from 5 to 25 bar or more. In these processes, cyclohexane is oxidized by air in the presence or absence of catalyst to give cyclohexyl hydroperoxide intermediate, and the cyclohexyl hydroperoxide successively undergoes thermal decomposition to form cyclohexanone and cyclohexanol. Because cyclohexanone and cyclohexanol are more oxidizable than cyclohexane, a large quantity of by-products is obtained in the oxidation stage. In order to reduce the proportion of undesired by-products, it is necessary to control the degree of conversion of cyclohexane.

TW Patent 150309 discloses a method for oxidizing cyclohexane in liquid phase. In this method, a high conversion of cyclohexane is achieved in a bubble reactor containing cycloaliphatic acid cobalt salts that act as catalyst under a condition of limited oxygen molecules dissolved in the liquid phase. U.S. Pat. No. 4,341,907 teaches an oxidation reaction of cyclohexane in the presence of a high concentration of cobalt salt catalysts greater than 0.1%. However, the conversion obtained by such a method is not satisfactorily improved. U.S. Pat. No. 4,658,056 discloses using a cobalt compound with ligands that act as first metal catalyst and cobalt naphthenate that act as second metal catalyst to perform the catalytic oxidation reaction of cyclohexane so as to increase the yield of products. But, such a two-catalyst system offers no advantage of reducing cost and simplifying operation.

It is already known the conversion of cyclohexane must be maintained low so as to increase the reaction selectivity for preparing cyclohexanone and cyclohexanol target products. However, a drawback of low conversion is that a large quantity of unreacted cyclohexane is circulated in the operation units, and this causes large energy consumption and can't fulfill economic requirement.

Therefore, it is desired to provide a method for efficiently oxidizing cyclohexane in liquid phase with simple operations and low costs.

To overcome the above-mentioned problems, the present invention has been accomplished after the present inventors made extensive researches and improvements.

SUMMARY OF THE INVENTION

It is an object of this invention to provide a method for oxidizing a hydrocarbon in liquid phase with a higher degree of conversion of raw material.

Another object of this invention is to provide a method for oxidizing a hydrocarbon in liquid phase with high reaction selectivity.

Further an object of this invention is to provide a method for oxidizing a hydrocarbon in liquid phase with an improved overall yield of products.

To achieve the aforementioned and other objects, a method for oxidizing a hydrocarbon in liquid phase is provided in the present invention, which comprises using a pyridine, bipyridine, or phenanthroline compound capable of chelating metals as auxiliary agent to perform a liquid-phase oxidation reaction of a hydrocarbon in the presence of a molecular oxygen-containing gas and a transition metal catalyst.

Accordingly, the present invention has advantages of higher conversion in catalytic oxidation reaction and enhancing overall yields of products without sacrificing the reaction selectivity.

DETAILED DESCRIPTION OF THE PREFERED EMBODIMENTS

The character and efficacy of the present invention will be further described in details by referring to the following examples, but the present invention is not limited thereto.

The present method for oxidizing a hydrocarbon in liquid phase is to oxidize a cycloalkane with 3 to 12 carbon atoms in the presence of an oxygen-containing gas, such as oxygen gas or air, and a metal catalyst, such as group III B to VIII B transition metal (e.g., cobalt and chromium) compounds or complexes thereof by using a pyridine, bipyridine, or phenanthroline compound, which can chelate metals, as auxiliary agent to form cycloalkanone and/or cycloalkanol (for example, oxidizing cyclohexane to form cyclohexanone and/or cyclohexanol).

The first embodiment of the present invention is to use pyridine compound having a structure represented by formula (I) as auxiliary agent:

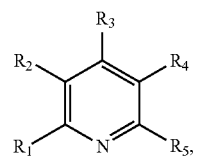

(I)

In formula (I), $R_1$, $R_2$, $R_3$, $R_4$, and $R_5$ are independently selected from the group consisting of hydrogen, halogen, nitro, cyano, hydroxy, carbonyl, carboxyl, amino, amido, $C_{1-6}$ alkyl, $C_{1-6}$ alkoxy, $C_{3-12}$ cycloalkyl, $C_{3-12}$ cycloalkoxy, $C_{3-12}$ cycloalkanoyl, $C_{6-20}$ aryl, $C_{7-20}$ arylalkyl, and $C_{7-20}$ alkylaryl, or $R_1$ and $R_2$, $R_2$ and $R_3$, or $R_3$ and $R_4$ may be joined mutually to form an aromatic or non-aromatic ring, which is optionally substituted with halogen, nitro, cyano, hydroxy, carbonyl, carboxyl, amino, and/or amido, wherein the $C_{1-6}$ alkyl, $C_{1-6}$ alkoxy, $C_{3-12}$ cycloalkyl, $C_{3-12}$ cycloalkoxy, $C_{3-12}$ cycloalkanoyl, $C_{6-20}$ aryl, $C_{7-20}$ arylalkyl, and $C_{7-20}$ alkylaryl are optionally substituted with halogen, nitro, cyano, hydroxy, carbonyl, carboxyl, amino, and/or amido. Preferably, $R_1$, $R_2$, $R_3$, $R_4$, and $R_5$ are independently selected from the group consisting of hydrogen, halogen, nitro, cyano, and carboxyl, or $R_1$ and $R_2$, $R_2$ and $R_3$, or $R_3$ and $R_4$ may be joined mutually to form an aromatic or non-aromatic ring, which is optionally substituted with halogen, nitro, cyano, and/or carboxyl.

The second embodiment of the present invention is to use bipyridine compound having a structure represented by formula (II) as auxiliary agent:

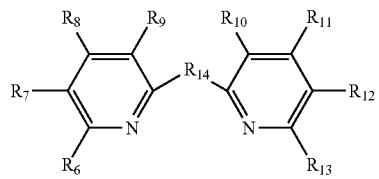

(II)

In formula (II), $R_6$, $R_7$, $R_8$, $R_9$, $R_{10}$, $R_{11}$, $R_{12}$ and $R_{13}$ are independently selected from the group consisting of hydrogen, halogen, nitro, cyano, hydroxy, carbonyl, carboxyl, amino, amido, $C_{1-6}$ alkyl, $C_{1-6}$ alkoxy, $C_{3-12}$ cycloalkyl, $C_{3-12}$ cycloalkoxy, $C_{3-12}$ cycloalkanoyl, $C_{6-20}$ aryl, $C_{7-20}$ arylalkyl, and $C_{7-20}$ alkylaryl, or $R_6$ and $R_7$, $R_7$ and $R_8$, $R_8$ and $R_9$, $R_9$ and $R_{10}$, and $R_{11}$, $R_{11}$ and $R_{12}$, or $R_{12}$ and $R_{13}$ may be joined mutually to form an aromatic or non-aromatic ring, which is optionally substituted with halogen, nitro, cyano, hydroxy, carbonyl, carboxyl, amino, and/or amido, wherein the $C_{1-6}$ alkyl, $C_{1-6}$ alkoxy, $C_{3-12}$ cycloalkyl, $C_{3-12}$ cycloalkoxy, $C_{3-12}$ cycloalkanoyl, $C_{6-20}$ aryl, $C_{7-20}$ arylalkyl, and $C_{7-20}$ alkylaryl are optionally substituted with halogen, nitro, cyano, hydroxy, carbonyl, carboxyl, amino, and/or amido; and $R_{14}$ represents chemical bond, bivalence oxy, ester group, ketone group, pyridonyl, $C_{1-6}$ alkyl, $C_{1-6}$ alkenyl, $C_{1-6}$alkylamino, $C_{1-6}$ alkoxy, $C_{1-6}$ alkanoyl, $C_{3-12}$ cycloalkyl, $C_{6-20}$ aryl, $C_{7-20}$ arylalkyl, or $C_{7-20}$ alkylaryl, wherein the $C_{1-6}$ alkyl and $C_{1-6}$ alkenyl are optionally substituted with halogen, nitro, cyano, hydroxy, carbonyl, carboxyl, amino, and/or amido. Preferably, $R_6$, $R_7$, $R_8$, $R_9$, $R_{10}$, $R_{11}$, $R_{12}$ and $R_{13}$ are independently selected from the group consisting of hydrogen, halogen, nitro, cyano, and carboxyl, or $R_6$ and $R_7$, $R_7$ and $R_8$, $R_8$ and $R_9$, $R_{10}$ and $R_{11}$, $R_{11}$ and $R_{12}$, or $R_{12}$ and $R_{13}$ may be joined mutually to form an aromatic or non-aromatic ring, which is optionally substituted with halogen, nitro, cyano, and/or carboxyl; and $R_{14}$ represents chemical bond, bivalence oxy, ester group, ketone group, pyridonyl, $C_{1-6}$ alkyl, or $C_{1-6}$ alkenyl, wherein the $C_{1-6}$ alkyl and $C_{1-6}$ alkenyl are optionally substituted with halogen, nitro, hydroxy, and/or amino.

The third embodiment of the present invention is to use phenanthroline compound having a structure represented by formula (III) as auxiliary agent:

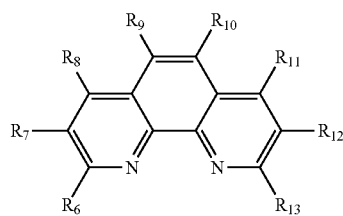

(III)

In formula (III), $R_6$, $R_7$, $R_8$, $R_9$, $R_{10}$, $R_{11}$, $R_{12}$ and $R_{13}$ are independently selected from the group consisting of hydrogen, halogen, nitro, cyano, hydroxy, carbonyl, carboxyl, amino, amido, $C_{1-6}$ alkyl, $C_{1-6}$ alkoxy, $C_{3-12}$ cycloalkyl, $C_{3-12}$ cycloalkoxy, $C_{3-12}$ cycloalkanoyl, $C_{6-20}$ aryl, $C_{7-20}$ arylalkyl, and $C_{7-20}$ alkylaryl, or $R_6$ and $R_7$, $R_7$ and $R_8$, $R_8$ and $R_9$, $R_9$ and $R_{10}$, $R_{10}$ and $R_{11}$, $R_{11}$, and $R_{12}$, or $R_{12}$ and $R_{13}$ may be joined mutually to form an aromatic or non-aromatic ring, which is optionally substituted with halogen, nitro, cyano, hydroxy, carbonyl, carboxyl, amino, and/or amido, wherein the $C_{1-6}$ alkyl, $C_{1-6}$ alkoxy, $C_{3-12}$ cycloalkyl, $C_{3-12}$ cycloalkoxy, $C_{3-12}$ cycloalkoxy, $C_{3-12}$ cycloalkanoyl, $C_{6-20}$ aryl, $C_{7-20}$ arylalkyl, and $C_{7-20}$ alkylaryl are optionally substituted with halogen, nitro, cyano, hydroxy, carbonyl, carboxyl, amino, and/or amido. Preferably, $R_6$, $R_7$, $R_8$, $R_9$, $R_{10}$, $R_{11}$, $R_{12}$ and $R_{13}$ are independently selected from the group consisting of hydrogen, halogen, nitro, cyano, and carboxyl, or $R_6$ and $R_7$, $R_7$ and $R_8$, $R_8$ and $R_9$, $R_9$ and $R_{10}$, $R_{10}$ and $R_{11}$, $R_{11}$, and $R_{12}$, or $R_{12}$ and $R_{13}$ may be joined mutually to form an aromatic or non-aromatic ring, which is optionally substituted with halogen, nitro, cyano, and/or carboxyl.

In the method of the present invention, the catalyst can be composed of metal ions or complex ions of cobalt or chromium, and the corresponding anions represented by formula (IV):

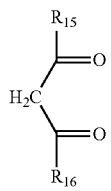

(IV)

In formula (III), $R_{15}$ and $R_{16}$ are independently selected from the group consisting of $C_{1-6}$ alkyl, $C_{3-12}$ cycloalkanoyl, $C_{6-20}$ aryl, $C_{7-20}$ arylalkyl, and $C_{7-20}$ alkylaryl, wherein the $C_{1-6}$ alkyl, $C_{3-12}$ cycloalkanoyl, $C_{6-20}$ aryl, $C_{7-20}$ arylalkyl, and $C_{7-20}$ alkylaryl are optionally substituted with halogen, nitro, hydroxy, alkoxycarbonyl, acyl, amino, and/or cyano. Preferably, $R_{15}$ and $R_{16}$ are independently selected from the group consisting of $C_{1-6}$ alkyl, $C_{6-20}$ aryl, $C_{7-20}$ arylalkyl, and $C_{7-20}$ alkylaryl.

In general, if the amount of a catalyst is insufficient, it leads to the low conversion of starting materials. Conversely, if the amount of the catalyst is excess, more by-products are given and production costs are also increased. Additionally, if the proportion of an auxiliary agent is too small, the auxiliary agent can't exert its effect. Conversely, if the proportion of the auxiliary agent is too large, it is not feasible to reduce costs. Therefore, in the method of the present invention, the concentration of a catalyst (calculated as metal ions) is usually in the range from 0.1 to 100 ppm by weight, preferably in the range from 0.5 to 20 ppm by weight, and the molar ratio of an auxiliary agent to a catalyst is normally in the range from 1:0.05 to 1:10, preferably in the range form 1:0.1 to 1:8.

Moreover, if the reaction pressure in the liquid-phase oxidation reaction is too low, it can cause an unstable reaction system, and in this case, it can't facilitate conversion increment. On the other hand, if the reaction pressure is too high, production costs can't be reduced. Typically, the reaction pressure is usually in the range from 4 to 20 kg/cm$^2$, preferably in the range from 6 to 14 kg/cm$^2$. Further, if the reaction temperature in the reaction system is too low, the oxidation reaction can't be carried out smoothly. On the other hand, if the reaction temperature is too high, it tends to increase the amount of by-products and is not in favor of the improvement of the reaction selectivity. Therefore, the reaction temperature in the present invention is normally at 120 to 180° C., preferably at 145 to 170° C.

EMBODIMENT EXAMPLES

The present invention is illustrated by the following Embodiment Examples, which do not limit the scope of the invention in any way.

Conversion, selectivity and yield, which were measured by acid-base titration, redox titration, and gas chromatography, were defined as the following equations:

Conversion (%)=the amount of cyclohexane converted (%)

Selectivity (%)=(the total amount of cyclohexyl hydroperoxide, cyclohexanol, and cyclohexanone produced/the amount of cyclohexane converted)×100%

Yield (%)=conversion×selectivity×100%

Comparative Example 1

In a stainless steel high-pressure reactor equipped with an agitator, 580.5 g (6.91 moles) of cyclohexanone was added. A nitrogen gas was introduced into the reactor to replace air therein until a pressure of 5 kg/cm² in the reactor was attained. The agitator was actuated and the temperature of the reaction system was heated to 155° C. Then, air was fed into the reactor to initiate an oxidation reaction. In the period of the reaction, the off-gases leaving the reactor were maintained at a flow rate of 900 ml/min and the pressure in the reactor was kept under 8 kg/cm². After the reaction was carried out for 80 minutes, the product thus-obtained was analyzed and its yield was calculated. The result is shown in Table 1.

Comparative Example 2

Comparative Example 1 was repeated, but using 5 ppm by weight (calculated as metal ions relative to cyclohexanone) of cobaltous chloride hexahydrate as catalyst. After having reacted for 80 minutes, the product thus-obtained was analyzed and its yield was calculated. The result is shown in Table 1.

Comparative Example 3

Comparative Example 1 was repeated, but using 0.02 moles of 2,6-di(2-pyridyl)-4(1H)-pyridone as auxiliary agent. After having reacted for 80 minutes, the product thus-obtained was analyzed and its yield was calculated. The result is shown in Table 1.

Embodiment Examples 1-2

Comparative Example 1 was repeated, but using 5 ppm by weight (calculated as metal ions relative to cyclohexanone) of cobalt metal ion as catalyst. A pyridine compound capable of chelating metal ions was also added as auxiliary agent according to Table 1 (catalyst and auxiliary agent in a molar ratio of 1:1). After having reacted for 80 minutes, the products thus-obtained were analyzed and their yields were calculated. The results are shown in Table 1.

Embodiment Examples 3-10

Comparative Example 1 was repeated, but using 5 ppm by weight (calculated as metal ions relative to cyclohexanone) of cobalt metal ion as catalyst. A bipyridine compound capable of chelating metal ions was also added as auxiliary agent according to Table 1 (catalyst and auxiliary agent in a molar ratio of 1:1). After having reacted for 80 minutes, the products thus-obtained were analyzed and their yields were calculated. The results are shown in Table 1.

Example 11

Comparative Example 1 was repeated, but using 5 ppm by weight (calculated as metal ions relative to cyclohexanone) of cobalt metal ion as catalyst. A phenanthroline compound capable of chelating metal ions was also added as auxiliary agent according to Table 1 (catalyst and auxiliary agent in a molar ratio of 1:1). After having reacted for 80 minutes, the product thus-obtained was analyzed and its yield was calculated. The result is shown in Table 1.

Embodiment Example 12

Example 11 was repeated, but using 5 ppm by weight (calculated as metal ions relative to cyclohexanone) of cobalt metal ion as catalyst, combined with 1-phenyl-1,3-butanedione as anion. After having reacted for 80 minutes, the product thus-obtained was analyzed and its yield was calculated. The result is shown in Table 1.

Embodiment Example 13

Comparative Example 1 was repeated, but using 5 ppm by weight (calculated as metal ions relative to cyclohexanone) of cobalt metal ion as catalyst. A phenanthroline compound with electron-donating substituents was also added as auxiliary agent according to Table 1 (catalyst and auxiliary agent in a molar ratio of 1:1). After having reacted for 80 minutes, the product thus-obtained was analyzed and its yield was calculated. The result is shown in Table 1.

TABLE 1

| | Catalyst | Auxiliary agent | Conversion % | Selectivity % | Yield % |
|---|---|---|---|---|---|
| Comparative Example 1 | — | — | 4.31 | 94.07 | 4.05 |
| Comparative Example 2 | cobaltous chloride hexahydrate | — | 5.69 | 89.48 | 5.09 |
| Comparative Example 3 | — | 2,6-di(2-pyridyl)-4(1H)-pyridone | 4.42 | 93.92 | 4.15 |
| Embodiment Example 1 | cobalt metal ion | 8-hydroxy-2-cyanobenzopyridine | 6.94 | 88.00 | 6.11 |
| Embodiment Example 2 | cobalt metal ion | 2-cyanopyridine | 9.23 | 87.08 | 8.05 |
| Embodiment Example 3 | cobalt metal ion | 2,2'-biquinoline | 8.87 | 86.61 | 7.68 |
| Embodiment Example 4 | cobalt metal ion | 2,2'-bipyridine | 7.98 | 87.65 | 6.99 |
| Embodiment Example 5 | cobalt metal ion | 2,2'-bipyridyl-3,3'-diol | 7.25 | 90.99 | 6.60 |
| Embodiment Example 6 | cobalt metal ion | 6,6'-dibromo-2,2'-bipyridine | 8.41 | 87.36 | 7.36 |
| Embodiment Example 7 | cobalt metal ion | 6,6'-diamino-2,2'-bipyridine | 7.12 | 89.17 | 6.35 |
| Embodiment Example 8 | cobalt metal ion | di (2-pyridyl)ketone | 7.12 | 88.97 | 6.33 |

TABLE 1-continued

| | Catalyst | Auxiliary agent | Conversion % | Selectivity % | Yield % |
|---|---|---|---|---|---|
| Embodiment Example 9 | cobalt metal ion | 1,2-di(2-pyridyl)-1,2-vinyldiol | 9.55 | 86.43 | 8.25 |
| Embodiment Example 10 | cobalt metal ion | 2,6-di(2-pyridyl)-4(1H)-pyridone | 9.52 | 84.33 | 8.07 |
| Embodiment Example 11 | cobalt metal ion | 1,10-phenanthroline | 6.74 | 88.21 | 5.95 |
| Embodiment Example 12 | cobalt metal ion with (1-phenyl-1,3-butanedione) anion | 1,10-phenanthroline | 8.64 | 88.01 | 7.60 |
| Embodiment Example 13 | cobalt metal ion | 4,7-diphenyl-1,10-phenanthroline | 4.98 | 91.42 | 4.55 |

As given in Table 1, the selectivity of the present invention was maintained higher than 84%. Compared to the liquid-phase oxidation reaction without a catalyst, the yield of the present invention was increased about 47 to 104%. Further, the increment of the yield was about 16 to 62% in comparison with using only cobaltous chloride hexahydrate as catalyst and free of auxiliary agent.

Additionally, when a specific anion was added in the catalytic system of this invention, the whole yield of the oxidation reaction can be further enhanced and the high selectivity of the reaction was still maintained.

Moreover, the results of Embodiment Examples show that as the auxiliary agent used in the present invention was substituted by electron-donating groups, the reaction selectivity tended to be increased, i.e., electron-releasing substituents had a good effect on the selectivity, even if the conversion of starting materials and the overall yield of products are lower.

Embodiment Examples 14-15

Example 10 was repeated, but adjusting the addition of the catalyst according to Table 2. After having reacted for 80 minutes, the products thus-obtained were analyzed and their yields were calculated. The results are shown in Table 2.

TABLE 2

| | Conc. of cobalt metal ion ppm | Conversion % | Selectivity % | Yield % |
|---|---|---|---|---|
| Embodiment Example 10 | 5 | 9.52 | 84.33 | 8.07 |
| Embodiment Example 14 | 0.5 | 8.79 | 84.71 | 7.45 |
| Embodiment Example 15 | 10 | 9.31 | 83.81 | 7.81 |

As shown in Table 2, in the case of a low catalyst concentration, the method of the present invention can also catalytically oxidize hydrocarbons in liquid phase very well, and the product yields can be significantly improved. Besides, the consumption of catalysts in the reaction processes can be reduced with an advantage of cost reduction.

Based on the results of the aforementioned Embodiment Examples, the present method, using a transition metal ion as catalyst in combination with an organic compound capable of chelating metals as auxiliary agent, can certainly improve the total oxidation yield and maintain the reaction selectivity above 80%. Moreover, when a specific anion is applied to the catalytic system of the present invention, the oxidation yield can be further increased.

The features and functions of the present invention have been elucidated in the foregoing detailed descriptions. Those skilled in the art will appreciate that modifications and variations according to the spirit and principle of the present invention may be made. All such modifications and variations are considered to fall within the spirit and scope of the present invention as defined by the appended claims.

What is claimed is:

1. A method for oxidizing hydrocarbon in liquid phase, comprising using a compound represented by formula (II) as an auxiliary agent to perform a liquid-phase oxidation reaction of the hydrocarbon in presence of an oxygen-containing gas and a cobalt halide as a catalyst:

(I)

wherein $R_6$, $R_7$, $R_8$, $R_9$, $R_{10}$, $R_{11}$, $R_{12}$ and $R_{13}$ are independently selected from the group consisting of hydrogen, halogen, nitro, cyano, hydroxy, carbonyl, carboxyl, amino, amido, $C_{1-6}$ alkyl, $C_{1-6}$ alkoxy, $C_{3-12}$ cycloalkyl, $C_{3-12}$ cycloalkoxy, $C_{3-12}$ cycloalkanoyl, $C_{6-20}$ aryl, $C_{7-20}$ arylalkyl, and $C_{7-20}$ alkylaryl, or $R_6$ and $R_7$, $R_7$ and $R_8$, $R_8$ and $R_9$, $R_{10}$ and $R_{11}$, $R_{11}$ and $R_{12}$, or $R_{12}$ and $R_{13}$ are joined mutually to form an aromatic or non-aromatic ring, which is optionally substituted with halogen, nitro, cyano, hydroxy, carbonyl, carboxyl, amino, and/or amido, wherein the $C_{1-6}$ alkyl, $C_{1-6}$ alkoxy, $C_{3-12}$ cycloalkyl, $C_{3-12}$ cycloalkoxy, $C_{3-12}$ cycloalkanoyl, $C_{6-20}$ aryl, $C_{7-20}$ arylalkyl, and $C_{7-20}$ alkylaryl are optionally substituted with halogen, nitro, cyano, hydroxy, carbonyl, carboxyl, amino, and/or amido, and $R_{14}$ represents chemical bond, oxy, ester group, ketone group, pyridonyl, $C_{1-6}$ alkyl, $C_{1-6}$ alkenyl, $C_{1-6}$ alkylamino, $C_{1-6}$ alkoxy, $C_{1-6}$ alkanoyl, $C_{3-12}$ cycloalkyl, $C_{6-20}$ aryl, $C_{7-20}$ arylalkyl, or $C_{7-20}$ alkylaryl, wherein the $C_{1-6}$ alkyl and $C_{1-6}$ alkenyl are optionally substituted with halogen, nitro, cyano, hydroxy, carbonyl, carboxyl, amino, and/or amido.

2. The method according to claim 1, wherein the $R_6$, $R_7$, $R_8$, $R_9$, $R_{10}$, $R_{11}$, $R_{12}$ and $R_{13}$ are independently selected from the group consisting of hydrogen, halogen, nitro, cyano, and carboxyl, or $R_6$ and $R_7$, $R_7$ and $R_8$, $R_8$ and $R_9$, $R_{10}$ and $R_{11}$, $R_{11}$ and $R_{12}$, or $R_{12}$ and $R_{13}$ are joined mutually to form an aromatic or non-aromatic ring, which is optionally substituted with halogen, nitro, cyano, and/or carboxyl, and $R_{14}$ represents chemical bond, oxy, ester group, ketone group, pyridonyl, $C_{1-6}$ alkyl, or $C_{1-6}$ alkenyl, wherein the $C_{1-6}$ alkyl and $C_{1-6}$ alkenyl are optionally substituted with halogen, nitro, hydroxy, and/or amino.

3. The method according to claim 1, wherein the hydrocarbon is cycloalkane with 3 to 12 carbon atoms.

4. The method according to claim 3, wherein the hydrocarbon is cyclohexane.

5. The method according to claim 1, wherein the catalyst is cobaltous chloride hexahydrate.

6. The method according to claim 1, wherein the catalyst has a concentration of from 0.1 to 100 ppm by weight based on cobalt metal ions.

7. The method according to claim 6, wherein the catalyst has a concentration of from 0.5 to 20 ppm by weight based on cobalt metal ions.

8. The method according to claim 1, wherein the catalyst to the auxiliary agent has a molar ratio of from 1:0.05 to 1:10.

9. The method according to claim 8, wherein the catalyst to the auxiliary agent has a molar ratio of from 1:0.1 to 1:8.

10. The method according to claim 1, wherein the oxidation reaction is performed at a pressure of from 4 to 20 kg/cm$^2$.

11. The method according to claim 10, wherein the oxidation reaction is performed at a pressure of from 6 to 14 kg/cm$^2$.

12. The method according to claim 1, wherein the oxidation reaction is performed at a temperature of from 120 to 180° C.

13. The method according to claim 12, wherein the oxidation reaction is performed at a temperature of from 145 to 170° C.

14. A method for oxidizing hydrocarbon in liquid phase, comprising using a compound represented by formula (III) as an auxiliary agent to perform a liquid-phase oxidation reaction of the hydrocarbon in presence of an oxygen-containing gas and a cobalt halide as a catalyst:

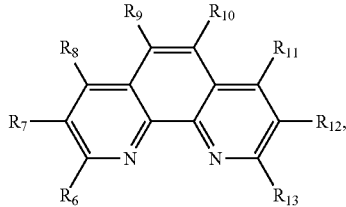

(III)

wherein $R_6$, $R_7$, $R_8$, $R^9$, $R_{10}$, $R_{11}$, $R_{12}$ and $R_{13}$ are independently selected from the group consisting of hydrogen, halogen, nitro, cyano, hydroxy, carbonyl, carboxyl, amino, amido, $C_{1-6}$ alkyl, $C_{1-6}$ alkoxy, $C_{3-12}$ cycloalkyl, $C_{3-12}$ cycloalkoxy, $C_{3-12}$ cycloalkanoyl, $C_{6-20}$ aryl, $C_{7-20}$ arylalkyl, and $C_{7-20}$ alkylaryl, or $R_6$ and $R_7$, $R_7$ and $R_8$, $R_8$ and $R_9$, $R_9$ and $R_{10}$, $R_{10}$ and $R_{11}$, $R_{11}$ and $R_{12}$, or $R_{12}$ and $R_{13}$ are joined mutually to form an aromatic or non-aromatic ring, which is optionally substituted with halogen, nitro, cyano, hydroxy, carbonyl, carboxyl, amino, and/or amido, wherein the $C_{1-6}$ alkyl, $C_{1-6}$ alkoxy, $C_{3-12}$ cycloalkyl, $C_{3-12}$ cycloalkoxy, $C_{3-12}$ cycloalkanoyl, $C_{6-20}$ aryl, $C_{7-20}$ arylalkyl, and $C_{7-20}$ alkylaryl are optionally substituted with halogen, nitro, cyano, hydroxy, carbonyl, carboxyl, amino, and/or amido.

15. The method according to claim 14, wherein the $R_6$, $R_7$, $R_8$, $R_9$, $R_{10}$, $R_{11}$, $R_{12}$ and $R_{13}$ are independently selected from the group consisting of hydrogen, halogen, nitro, cyano, and carboxyl, or $R_6$ and $R_7$, $R_7$ and $R_8$, $R_8$ and $R_9$, $R_9$ and $R_{10}$, $R_{10}$ and $R_{11}$, $R_{11}$ and $R_{12}$, or $R_{12}$ and $R_{13}$ are joined mutually to form an aromatic or non-aromatic ring, which is optionally substituted with halogen, nitro, cyano, and/or carboxyl.

16. The method according to claim 14, wherein the hydrocarbon is cycloalkane with 3 to 12 carbon atoms.

17. The method according to claim 16, wherein the hydrocarbon is cyclohexane.

18. The method according to claim 14, wherein the catalyst is cobaltous chloride hexahydrate.

19. The method according to claim 14, wherein the catalyst has a concentration of from 0.1 to 100 ppm by weight based on cobalt metal ions.

20. The method according to claim 19, wherein the catalyst has a concentration of from 0.5 to 20 ppm by weight based on cobalt metal ions.

21. The method according to claim 14, wherein the catalyst to the auxiliary agent has a molar ratio of from 1:0.05 to 1:10.

22. The method according to claim 21, wherein the catalyst to the auxiliary agent has a molar ratio of from 1:0.1 to 1:8.

23. The method according to claim 14, wherein the oxidation reaction is performed at a pressure of from 4 to 20 kg/cm$^2$.

24. The method according to claim 23, wherein the oxidation reaction is performed at a pressure of from 6 to 14 kg/cm$^2$.

25. The method according to claim 14, wherein the oxidation reaction is performed at a temperature of from 120 to 180° C.

26. The method according to claim 25, wherein the oxidation reaction is performed at a temperature of from 145 to 170° C.

* * * * *